US009730982B2

(12) United States Patent
McKay et al.

(10) Patent No.: US 9,730,982 B2
(45) Date of Patent: *Aug. 15, 2017

(54) MALLEABLE MULTI-COMPONENT IMPLANTS AND MATERIALS THEREFOR

(71) Applicant: WARSAW ORTHOPEDIC INC., Warsaw, IN (US)

(72) Inventors: William F. McKay, Memphis, TN (US); Jeffrey L. Scifert, Arlington, TN (US); Kathy Remsen, Germantown, TN (US); Didier Billy, Maastricht (NL); Mirian Gillissen, Gulpen (NL); Scott M. Vickers, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,957

(22) Filed: Sep. 22, 2014

(65) Prior Publication Data

US 2015/0011472 A1    Jan. 8, 2015

Related U.S. Application Data

(63) Continuation of application No. 12/056,549, filed on Mar. 27, 2008, now Pat. No. 8,840,913.

(51) Int. Cl.
*A61K 38/18* (2006.01)
*A61K 9/00* (2006.01)
*A61L 27/26* (2006.01)
*A61L 27/54* (2006.01)

(52) U.S. Cl.
CPC ........ *A61K 38/1875* (2013.01); *A61K 9/0024* (2013.01); *A61L 27/26* (2013.01); *A61L 27/54* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,394,370 A | 7/1983 | Jefferies |
| 4,430,760 A | 2/1984 | Smestad |
| 4,440,750 A | 4/1984 | Glowacki |
| 4,472,840 A | 9/1984 | Jefferies |
| 4,485,097 A | 11/1984 | Bell |
| 4,722,948 A | 2/1988 | Sanderson |
| 4,776,890 A | 10/1988 | Chu |
| 4,789,663 A | 12/1988 | Wallace |
| 4,863,732 A | 9/1989 | Nathan |
| 4,891,359 A * | 1/1990 | Saferstein ............ A61L 24/0015 424/499 |
| 5,162,114 A | 11/1992 | Kuberasampath |
| 5,275,954 A | 1/1994 | Wolfinbarger |
| 5,284,655 A | 2/1994 | Bogdansky |
| 5,290,558 A | 3/1994 | O'Leary |
| 5,298,254 A | 3/1994 | Prewett |
| 5,314,476 A | 5/1994 | Prewett |
| 5,356,629 A | 10/1994 | Sander |
| 5,405,390 A | 4/1995 | O'Leary |
| 5,439,684 A | 8/1995 | Prewett |
| 5,510,396 A | 4/1996 | Prewett |
| 5,513,662 A | 5/1996 | Morse |
| 5,516,532 A | 5/1996 | Atala |
| 5,531,791 A | 7/1996 | Wolfinbarger |
| 5,707,962 A | 1/1998 | Chen |
| 5,711,957 A | 1/1998 | Patat |
| 5,739,286 A | 4/1998 | Silver |
| 5,866,165 A * | 2/1999 | Liu .................. A61L 27/24 424/486 |
| 5,925,736 A | 7/1999 | Neff |
| 5,948,426 A | 9/1999 | Jefferies |
| 6,030,635 A | 2/2000 | Gertzman |
| 6,124,273 A | 9/2000 | Drohan |
| 6,165,487 A | 12/2000 | Ashkar |
| 6,180,606 B1 | 1/2001 | Chen |
| 6,197,325 B1 | 3/2001 | MacPhee |
| 6,200,606 B1 | 3/2001 | Peterson |
| 6,214,368 B1 | 4/2001 | Lee |
| 6,281,195 B1 | 8/2001 | Rueger |
| 6,287,341 B1 | 9/2001 | Lee |
| 6,293,970 B1 | 9/2001 | Wolfinbarger |
| 6,294,187 B1 | 9/2001 | Boyce |
| 6,297,213 B1 | 10/2001 | Oppermann |
| 6,309,659 B1 | 10/2001 | Clokie |
| 6,311,690 B1 | 11/2001 | Jefferies |
| 6,326,018 B1 | 12/2001 | Gertzman |
| 6,328,765 B1 | 12/2001 | Hardwick |
| 6,331,312 B1 | 12/2001 | Lee |
| 6,340,477 B1 | 1/2002 | Anderson |
| 6,346,515 B1 | 2/2002 | Pitaru |
| 6,368,356 B1 | 4/2002 | Zhong |
| 6,372,257 B1 * | 4/2002 | Marchosky ............... 424/422 |
| 6,437,018 B1 | 8/2002 | Gertzman |
| 6,458,375 B1 | 10/2002 | Gertzman |
| 6,679,918 B1 | 1/2004 | Benedict |

(Continued)

FOREIGN PATENT DOCUMENTS

WO         9835653 A1    8/1998
WO    WO 0045870 A1 *   8/2000   ......... A61K 38/1875

OTHER PUBLICATIONS

International Search Report and Written Opinion for US Application PCT/US2009/036988 mailed on Mar. 5, 2010.
OP-1 Putty, Package Insert, Stryker Biotech, LLC, 2004.

*Primary Examiner* — Susan Tran
*Assistant Examiner* — William Craigo (57) ABSTRACT

Described are implantable, malleable medical materials comprising mineral particles, insoluble collagen fibers, and a gel-forming polysaccharide component and/or another added gel-former. The malleable medical materials can be used treat bone or other tissue defects in patients, including in conjunction with biologically active factors such as osteogenic proteins. Also described are methods and materials that can be used to prepare the malleable medical materials.

4 Claims, 2 Drawing Sheets

(56) References Cited

U.S. PATENT DOCUMENTS

| | | |
|---|---|---|
| 2001/0014667 A1 | 8/2001 | Chen |
| 2001/0018614 A1 | 8/2001 | Bianchi |
| 2002/0018796 A1 | 2/2002 | Wironen |
| 2002/0034531 A1 | 3/2002 | Clokie |
| 2002/0071827 A1 | 6/2002 | Petersen |
| 2002/0072804 A1 | 6/2002 | Donda |
| 2002/0076429 A1 | 6/2002 | Wironen |
| 2002/0082694 A1 | 6/2002 | McKay |
| 2002/0082697 A1 | 6/2002 | Damien |
| 2002/0098222 A1 | 7/2002 | Wironen |
| 2002/0151985 A1 | 10/2002 | Kuberasampath |
| 2003/0049328 A1* | 3/2003 | Dalal .................. A61L 27/12 424/602 |
| 2003/0236573 A1 | 12/2003 | Evans |
| 2004/0002558 A1 | 1/2004 | McKay |
| 2004/0034434 A1 | 2/2004 | Evans |
| 2004/0062816 A1 | 4/2004 | Atkinson |
| 2004/0064193 A1 | 4/2004 | Evans |
| 2004/0127987 A1 | 7/2004 | Evans |
| 2004/0138758 A1 | 7/2004 | Evans |
| 2004/0230309 A1 | 11/2004 | DiMauro |
| 2005/0084542 A1* | 4/2005 | Rosenberg ............ A61L 27/227 424/549 |
| 2005/0186240 A1 | 8/2005 | Ringeison |
| 2007/0190083 A1 | 8/2007 | Scifert et al. |
| 2007/0254042 A1 | 11/2007 | Drapeau |

* cited by examiner

MALLEABLE MULTI-COMPONENT IMPLANTS AND MATERIALS THEREFOR

This application is a divisional application of U.S. patent application Ser. No. 12/056,549, filed Mar. 27, 2008, and entitled "MALLEABLE MULTI-COMPONENT IMPLANTS AND MATERIALS THEREFOR." This entire disclosure is incorporated herein by reference into the present disclosure.

BACKGROUND OF THE INVENTION

The present invention relates generally to medical putty implant materials, and in certain aspects to medical putty implant materials containing collagen and other components.

A variety of materials have been suggested for the treatment of bone defects. In addition to traditional bone grafting, a number of synthetic bone graft substitutes have been used or explored, including several putty materials.

To conduct bone through-growth effectively, implant materials derive benefit from the presence of substantial scaffolding material such as biocompatible ceramics or other mineral scaffolds. Such mineral materials are generally hard, brittle substances. The incorporation of substantial levels of mineral particles into putty materials, particularly in respect of granules or other relatively large particles, proves difficult because the large pieces of hard mineral tend to disrupt the putty mass such that it is readily broken or eroded away, and lacks cohesiveness desired for handling prior to implant and for persistence after implant. This may present problems in achieving effective bone growth into and through the desired implant volume, due to migration or separation of the scaffolding particulates.

In view of the background in the area, there exist needs for improved putty materials which have incorporated mineral particles while maintaining the desired combination of malleability and cohesiveness. In certain aspects, the present invention is directed to these needs.

SUMMARY

In certain of its aspects, the present invention relates to malleable medical implant formulations that include insoluble collagen particles and mineral particles combined with a liquid phase that includes at least one gel-forming agent, which in advantageous forms is a polysaccharide compound. Accordingly, in certain embodiments, the invention provides an implantable medical material comprising a malleable medical putty that includes mineral particles, insoluble collagen particles, and a polysaccharide component including one or more polysaccharide compounds. The malleable medical putty is desirably a cohesive, shape-retaining putty. Such a putty can for example be comprised about 40% to about 75% by weight of a liquid aqueous medium, and in certain embodiments about 60% to about 75% of a liquid aqueous medium. Also, the putty can include a bone morphogenic protein, for instance incorporated at a level of about 0.6 milligrams per cubic centimeter (mg/cc) to about 2 mg/cc. The mineral particles in the putty can have an average particle diameter in the range of about 0.4 millimeters (mm) to about 5 mm, and can be incorporated at a level of about 0.25 g/cc to about 0.55 g/cc in the overall putty. The putty can further include the insoluble collagen particles at a level of about 0.04 g/cc to about 0.15 g/cc, the soluble collagen at a level of about 0.01 g/cc to about 0.08 g/cc, and the polysaccharide at a level of about 0.01 to about 0.20 g/cc. The weight ratio of insoluble collagen fibers to soluble collagen in the putty can be in the range of about 4:1 to about 1:1, and/or the weight ratio of soluble collagen to the polysaccharide component (including the sum of the one or more polysaccharides present) in the putty can be in the range of about 4:1 to about 1:4.

In another embodiment, the invention provides a method for preparing an implantable medical putty material. The method includes providing a dry, porous material that includes a particulate mineral material having an average particle diameter of about 0.4 mm to about 5 mm embedded within a disruptable matrix. The disruptable matrix comprises a combination including insoluble collagen particles and a polysaccharide component including one or more polysaccharide compounds. An amount of an aqueous medium is applied to the dry, porous material and the material is disrupted to form a malleable implant material. In certain forms, the dried material is comprised about 70% to about 90% by weight of the particulate mineral material, about 10% to about 30% by weight of the insoluble collagen particles, and about 1% to about 20% of the polysaccharide component. In certain embodiments, the collagenous matrix includes insoluble collagen particles and soluble collagen present in a weight ratio of 4:1 to about 1:1, and the soluble collagen and polysaccharide component in a weight ratio of about 4:1 to about 1:4. The aqueous liquid medium can be added in an amount sufficient to constitute about 40% to 75% by weight of the overall putty, and in certain embodiments about 60% to 75% by weight of the overall putty. In certain aspects, the aqueous medium can include a bone morphogenic protein dissolved therein at a level of about 0.6 mg/cc to about 2 mg/cc, so as to result in an implantable osteogenic medical putty material.

In another embodiment, the invention provides a medical implant material that includes an aqueous gel carrier comprising a gel-forming alginate and at least one additional gel-forming agent. Insoluble collagen particles and mineral particles are in admixture with the aqueous gel carrier. Such implant materials can be prepared in accordance with methods of the invention which include adding an aqueous medium to a dry material, desirably a dried porous body, including the insoluble collagen particles, the mineral particles, the gel-forming alginate, and the at least one additional gel-forming agent. The at least one additional gel-forming agent can in certain embodiments include a starch that increases the viscosity of the aqueous gel carrier or a macromolecular substance that is effective in forming a thermally reversible gel, such as gelatin.

In still another embodiment, the invention provides an implant material that comprises a dried porous body including a particulate mineral material embedded within a matrix, wherein the matrix includes a combination of insoluble collagen particles at least one gel-forming agent, such as one or more polysaccharides, and at least one biocompatible wetting agent that enhances the rate of wetting of the dried porous body when contacted with an aqueous medium. The particulate mineral material can have an average particle diameter of about 0.4 mm to about 5 mm. The matrix can be disruptable upon wetting so as to be useful in the preparation of a putty. The body can comprise about 70% to about 90% by weight of the particulate mineral material, about 10% to about 30% by weight of the insoluble collagen, and about 1% to about 15% of the one or more polysaccharides or other gel-forming agents. The wetting agent can be an organic polyhydroxy compound, such as polyethylene glycol. In certain forms, the insoluble collagen particles and a polysaccharide component including one or more polysaccharide compounds are present in a weight ratio of about 4:1 to about 1:1. The dried porous body can be wettable with a biocompatible aqueous liquid to form a malleable, cohesive, shape-retaining putty material that includes the insoluble collagen particles and the mineral particles in admixture with an aqueous gel including the at least one gel-forming agent and the wetting agent.

In still further embodiments, the present invention provides methods for treating patients that involve implanting in the patients a medical material as described herein, and/or prepared as described herein.

Additional embodiments as well as features and advantages of the present invention will be apparent to those of ordinary skill in the art from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable malleable medical materials such as putties, and to methods and materials that are useful for preparing such materials. Preferred medical materials of the invention possess a combination of advantageous properties including high mineral content, malleability, cohesiveness, and shape retention. In this regard, as used herein the term "malleable" means that the material is capable of being permanently converted from a first shape to a second shape by the application of pressure. The term "cohesive" as used herein to describe a putty means that the putty tends to remain a singular, connected mass upon stretching, including the exhibition of the ability to elongate substantially without breaking upon stretching. In the context of stretching putties of the invention containing insoluble collagen fibers and polysaccharide, the advantageous putties exhibit elongation, during which the existence of substantial levels of intermeshed collagen fibers clinging to one another becomes apparent. As used herein, the term "shape-retaining" as used to describe a putty means that the putty is highly viscous and unless acted upon with pressure tends to remain in the shape in which it is placed. This is contrasted to thinner paste form materials which readily flow, and thus would pool or puddle upon application to a surface. In certain features of the invention, novel combinations of ingredients provide a medical putty material that not only contains a significant, high level of large particulate mineral particles, but also exhibits superior properties with respect to malleability, cohesiveness, and shape retention.

Malleable implant materials according to aspects of the present invention will include a combination of insoluble collagen, and one or more polysaccharides and/or another gel-forming agent ("GFA"). In certain embodiments, malleable implant materials of the invention will also include soluble collagen. In this regard, "soluble collagen" refers to the solubility of individual tropocollagen molecules in acidic aqueous environments. Tropocollagen may be considered the monomeric unit of collagen fibers and its triple helix structure is well recognized. Soluble collagen can beneficially be used in malleable compositions described herein to participate in forming a thickened liquid gel phase for admixture with implant solids. "Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, etc.) that is situated between the grain and the flesh sides. "Reconstituted collagen" is essentially collagen fiber segments that have been depolymerized into individual triple helical molecules, then exposed to solution and then reassembled into fibril-like forms.

In one aspect, a medical material is provided that contains both soluble collagen and insoluble collagen particles, e.g. fibers or randomized pieces. The soluble collagen and insoluble collagen fibers or other particles can first be prepared separately, and then combined. Both the soluble collagen and/or the insoluble collagen can be derived from bovine hides, but can also be prepared from other collagen sources (e.g. bovine tendon, porcine tissues, recombinant DNA techniques, fermentation, etc.). Human collagen can also be used in compositions described herein, including for example human tissue-derived collagen from tendon, skin or fascia, or other sources. Recombinant human collagen can also be used.

The liquid phase of malleable medical implant compositions in accordance with certain aspects of the invention will comprise a polysaccharide component including one or a plurality of polysaccharide compounds. Desirably, the polysaccharide component is included in an amount that increases the viscosity of the liquid phase or that otherwise improves the cohesiveness of a wetted insoluble collagen/soluble collagen/particulate mineral admixture. In addition, the polysaccharide component can serve to plasticize the insoluble collagen/mineral particle mixture so as to improve the flow properties and/or reduce the tackiness of the overall malleable composition.

Polysaccharides that can be used alone or in combination in the polysaccharide component include, for example, alginate, hyaluronic acid, chondroitin sulfate, dextran, dextran sulfate, heparin, heparin sulfate, chitosan, gellan gum, xanthan gum, guar gum, and K-carrageenan, starch (e.g. potato starch, wheat starch, or corn starch), or mixtures of two or more of these or other polysaccharides. The gel-forming agent can also be a gel-forming polypeptide, including thermally reversible gel forming polypeptides such as gelatin. In certain embodiments, gelatin or another thermally reversible gel forming agent that has a gel temperature at or slightly above human body temperature (about 37° C.) can be used in addition to or as an alternative to the polysaccharide compound(s). In this manner, the thermally reversible gel forming agent can be used in amounts which thicken the fluid carrier component of the malleable implant material at temperatures below body temperature, and the fluid component will not suffer a significant decrease in viscosity owing to thermal reversal of the gel (because the thermally reversible gel forming agent remains substantially at or below its gel temperature). In other embodiments utilizing gelatin or other thermally reversible gel forming agent with a gel temperature at or above body temperature, the malleable formulation can be heated to a temperature above body temperature to increase its flowability (preferably only slightly thereabove, e.g. about 38-40° C.), and then implanted in a patient, including a human patient. The gelatin or other thermally reversible gel forming agent will then cool and gel, thus enhancing the integrity of the implanted malleable mass at the implant site.

In certain embodiments, the malleable formulations contain at least one ionic polysaccharide that is capable of forming a thermally irreversible ionically-crosslinked gel upon combination with monovalent, divalent or other polyvalent ionic species, in many cases a cationic species. Ionically crosslinkable materials contemplated for use in the practice of the present invention include ionic materials such as alginates, chitosan, gellan gum, xanthan gum, hyaluronic acid, heparin, pectin, carrageenan, and the like. Many suitable polysaccharides are plant-derived polysaccharides, such as alginates and pectins (including gel-forming derivatives thereof). Other suitable polysaccharides can be derived from bacteria, for example gellan gums that are derived from *Pseudomonas elodea*.

Aqueous solutions of ionic polysaccharides can generally form ionically-crosslinked gels upon contact with aqueous solutions of counter-ions. For instance, useful agents for ionically crosslinking alginate, pectin and other similar polysaccharides include cationic gelling agents, preferably including divalent or trivalent cations. Useful divalent cations for these purposes include the alkaline earth metals, especially calcium and strontium. Aluminum is a useful crosslinking trivalent cation. These ionic crosslinking agents will usually be provided by salts. Useful anionic counterions for the calcium or other salts are desirably selected from pharmaceutically-acceptable anions such as chlorides, gluconates, fluorides, citrates, phosphates, tartrates, sulphates, acetates, borates, and the like. An especially preferred ionic crosslinking agent for use with an alginate or pectin compound is provided by calcium chloride. The ionic polysaccharide chitosan can also be used, and can be ionically crosslinked with multivalent, anionic gelling agents. Such agents include metal polyphosphates, such as an alkali metal or ammonium polyphosphate, pyrophosphates or metaphosphates. Citrates can also be used. These anionic crosslinking agents will also usually be provided by salts. The cationic counter-ion for the polyphosphate or other salt can be any suitable, biocompatible or pharmaceutically-acceptable cation including for instance sodium, potassium, or ammonium. Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations, such as gellan gums, can also be used. Such polysaccharides may form gels upon exposure, for example, to a solution comprising physiological levels of sodium. Many other biocompatible polysaccharides, including plant-derived and animal-derived materials, as well as corresponding ionic crosslinking agents, are known and can also be used in aspects of the present invention.

While the use of those ionic polysaccharides that are capable of forming thermally-irreversible ionically-crosslinked gels is preferred, it will be understood that in the present invention these polysaccharides will be ionically crosslinked, if at all, only to an extent that does not eliminate the malleable nature of the implant material. Thus, within aspects of the present invention, no or substantially no ionic crosslinking agent will be added, or in some cases only a relatively small amount of ionic crosslinking agent can be added in order to increase the viscosity of the overall formulation. On the other hand, in other aspects of the invention, malleable compositions as described herein can be contacted with an amount of a liquid medium containing an ionic crosslinking agent immediately prior to, during, or after implantation of the material into a patient. Illustratively, a malleable composition as described herein can be co-administered with a liquid medium of ionic crosslinker, as in the case of a dual-barrel syringe administration by which the malleable composition and crosslinker are admixed as they exit the syringe. Alternatively, a previously-implanted amount of the malleable composition can be washed with a solution or other liquid medium containing an appropriate ionic crosslinking agent to stiffen the implanted material in situ.

In certain embodiments, putty-form compositions include the insoluble collagen fibers at a level of 0.04 g/cc to 0.15 g/cc of the putty, and the total GFA (e.g. polysaccharide(s) and/or gelatin) at a level of 0.01 g/cc to 0.20 g/cc of the putty. In other embodiments, such compositions include insoluble collagen fibers at a level of about 0.05 to 0.1 g/cc in the putty, and optionally also soluble collagen and polysaccharide(s) each at a level of about 0.02 to about 0.05 g/cc in the putty. Advantageous putties can include insoluble collagen fibers in an amount (percent by weight) that is at least equal to or greater than the total amount of GFA, to contribute beneficially to the desired handling and implant properties of the putty material. In further embodiments, the putty will include insoluble collagen fibers and total GFA present in a weight ratio of 4:1 to 1:1. In still further embodiments, the putty will include soluble collagen and a polysaccharide component (including one or more polysaccharides) in a weight ratio of 4:1 to 1:4, including putties that include insoluble collagen fibers and soluble collagen in a weight ratio of about 75:25 to about 60:40, and soluble collagen and the polysaccharide component in a weight ratio of about 2:1 to 1:2. Further still, additional desired putties of the invention include the insoluble collagen fibers and soluble collagen in a weight ratio of about 75:25 to about 65:35, and the soluble collagen and polysaccharide(s) in a weight ratio of about 2:1 to 1:2, and in certain specific embodiments the weight ratio of insoluble collagen to soluble collagen will be about 70:30 and while that of the soluble collagen to polysaccharide(s) remains in the range of about 1:2 to 2:1.

Medical putties or other compositions of the present invention also include an amount of a particulate mineral material. In certain aspects of the invention, the particulate mineral is incorporated in the inventive putty composition at a level of at least about 0.25 g/cc of putty, and typically in the range of about 0.25 g/cc to about 0.55 g/cc. Such relatively high levels of mineral can be helpful in providing a scaffold for the ingrowth of new bone.

The mineral used in the present invention can include a natural or synthetic mineral or mixture of mineral materials that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The mineral material can be particulate having an average particle diameter between about 0.4 and 5.0 mm, more typically between about 0.4 and 3.0 mm, and desirably between about 0.4 and 2.0 mm.

In another aspect of the invention, the mineral material can include bone particles, possibly cancellous but preferably cortical, ground to provide an average particle diameter among those discussed above for the particulate mineral material. Both human and non-human sources of bone are suitable for use in the instant invention, and the bone may be autograft, allograft or xenograft in nature relative to the mammal to receive the implant. Appropriate pre-treatments known in the art may be used to minimize the risks of disease transmission and/or immunogenic reaction when using bone particles as or in the mineral material. Such bone particles can be used alone or in combination with synthetic mineral materials as described herein.

In one embodiment, xenogenic bone that has been pre-treated to reduce or remove its immunogenicity is used in or as the porous mineral matrix in the implant composition. For example, the bone can be calcined or deproteinized to reduce the risks of immunogenic reactions to the implant material.

A putty-form composition of the invention can include a significant proportion of a liquid carrier, which will generally be an aqueous liquid such as water, saline, or buffered solution. In one aspect, a malleable, cohesive, shape-retaining putty of the invention comprises about 60% to 75% by weight of an aqueous liquid medium, such as water. It will be understood however that higher or lower levels of the liquid medium can also be used to prepare either firmer (e.g. dampened solid matrices) or more flowable materials, such as pastes, for implantation in a patient. As will also be appreciated by those skilled in the art, the pH, ionic strength, and other characteristics of the liquid carrier medium can be selected to control or modulate the viscosity imparted the GFA. Illustratively, these and other parameters of the liquid component can be controlled to prevent undesired levels of ionic crosslinking of any polysaccharide(s) present that would unduly disrupt the malleable character of preferred implant compositions.

Malleable compositions described herein can also include a bone morphogenic protein or another osteogenic substance incorporated therein in an effective amount to render the composition osteogenic when implanted in a mammal, such as a human patient. In one embodiment, an inventive putty composition includes a bone morphogenic protein or other similar osteogenic protein at a level of about 0.6 milligrams per cubic centimeter (mg/cc) of putty to about 2 mg/cc of putty, advantageously at a level of about 0.8 mg/cc to about 1.8 mg/cc.

As noted above, in certain embodiments, compositions of the invention will incorporate at least as much insoluble collagen fiber as total GFA on a weight basis, e.g. in a weight ratio of about 4:1 to about 1:1. In some forms, putty compositions will include insoluble collagen fibers and soluble collagen, with more insoluble collagen fibers than soluble collagen being present, for instance, in a weight ratio of about 75:25 to about 60:40, more desirably about 75:25 to about 65:35, and in one specific embodiment about 70:30. Suitable collagen materials for these purposes can be prepared using techniques known in the literature or can be obtained from commercial sources, including for example from Kensey Nash Corporation (Exton, Pa.) which manufactures soluble collagen known as Semed S, fibrous collagen known as Semed F, and a composite collagen known as P1076.

Any suitable osteogenic material can be used in methods and/or compositions of the invention, including for instance harvested autologous bone or other suitable osteogenic substances. In certain embodiments, the osteogenic substance can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products (biologically active fragments) thereof. These proteins can be used individually or in mixtures of two or more. rhBMP-2 or biologically active derivatives or fragments thereof that exhibit an ability to induce bone growth are preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed. In certain embodiments, the amount of osteogenic protein to be delivered to the implant site will be in a range of from about 0.05 to about 1.5 mg.

Other therapeutic growth factors or substances may also be used in putties or other malleable compositions of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β. As well, other biologically-derived matrix materials such as demineralized bone matrix (DBM) may be incorporated into putties of the invention.

The osteogenic proteins or other biologically active agents to be used in the present invention can be provided in liquid formulations, for example buffered aqueous formulations. In certain embodiments, such formulations are mixed with, received upon and/or within, or otherwise combined with a dried implant material which is then manipulated to prepare a malleable osteogenic material of the invention.

As further enhancements of the compositions of the present invention, those skilled in the art will readily appreciate that other osteogenic enhancing factors may be incorporated into the composition. Such additional factors include, but are not limited to host compatible osteogenic progenitor cells, autograft bone marrow, allograft bone marrow, transforming growth factor-beta, fibroblast growth factor, platlet derived growth factor, insulin-like growth factor, microglobulin-beta, antibiotics, antifungal agents, wetting agents, glycerol, steroids and non-steroidal anti-inflammatory compounds.

In another aspect, the present invention provides a dry implant material that can be combined with an appropriate amount of an aqueous medium in order to prepare putty materials. The dry implant material can be in any suitable form, including for example a mixed powder. In advantageous forms, the dry implant material will be a porous body that includes a particulate mineral material embedded within a disruptable matrix, with the particulate mineral material desirably having an average particle diameter of about 0.4 mm to about 5.0 mm. The dried, porous implant body or other dry material can be comprised about 70% to about 90% by weight of the particulate mineral material, about 10% to about 30% by weight of insoluble collagen particles, and about 1% to about 15% by weight of the polysaccharide(s) and/or other additional gel-forming component. When both insoluble and soluble collagens are used, of the combined collagens, the dried porous body or other material can include about 1% to 25% by weight of insoluble collagen and about 1% to 15% by weight of soluble collagen, more preferably about 8% to about 20% by weight of the insoluble collagen and about 2% to about 12% of the soluble collagen. In certain embodiments, the dried, porous implant body or other material can include the total GFA in an amount from about 6% to about 10% by weight.

Dried implant bodies as described herein can also include an amount of an agent that enhances the rate of wetting of the dried material by aqueous mediums. For example, the wetting agent can be a biocompatible organic polyhydroxy compound having a molecular weight that is lower than that of the polysaccharide or other gel-forming agent. Illustratively, the biocompatible wetting agent can be a polyol compound, such as polyethylene glycol polymer, having a molecular weight of less than about 10,000, for example in the range of about 500 to about 5000 in certain embodiments. Such a wetting agent can constitute about 1% to about 25% by weight of the implant body on a dry weight basis. Especially in the case of relatively hydrophobic polysaccharides that resist wetting, such as alginates, it has been found that the incorporation of a biocompatible wetting agent significantly enhances the formation of a malleable material by adding an aqueous medium to a dried implant body or other dry material as described herein. Dried implant bodies that include a mixture of starch and alginate have also been found to wet more readily than those with alginate alone, and can optionally include a mixture of all three of a starch, an alginate, and a biocompatible wetting agent as described above.

Dried porous bodies having compositions as described herein can also be non-disruptable three-dimensional bodies, not susceptible in the wetted condition to manual crushing and kneading to form a putty or other conformable material, but rather are sustained as a single, integral piece. Such devices may be rigid or may exhibit shape memory, for example including sponge or foam devices. These non-disruptable bodies, or disruptable bodies, can optionally be implanted as bodies in dry form, or in a wetted condition. As well, such disruptable or non-disruptable bodies can be treated with or contain bioactive agents or mixtures thereof as described herein.

Considering components on a weight ratio basis, the porous body or other dry material (and malleable compositions when prepared therefrom) can include insoluble collagen particles and GFA present in a weight ratio of 4:1 to 1:1, advantageously about 75:25 to about 60:40. Additionally or alternatively, the porous body or other dry material can include the soluble collagen and polysaccharide or other GFA component in a weight ratio of about 4:1 to about 1:4, advantageously about 2:1 to about 1:2. In addition, as discussed above, the particulate mineral material can have an average particle diameter between 0.4 and 3.0 mm, and more desirably between 0.4 and 2.0 mm.

In certain embodiments, a dried, porous body as discussed above can have a density of between about 0.1 g/cc to about 0.3 g/cc, more desirably between about 0.15 g/cc and about 0.25 g/cc, and in certain aspects between about 0.18 g/cc and about 0.25 g/cc. Such dried, porous implant bodies can also exhibit porosities of at least about 50%, more desirably at least about 70% up to about 90%, and in certain embodiments in the range of about 80% to about 90%.

Dried, porous implant bodies in accordance with the invention can be provided in any suitable shape, including cylinders, cubes, chunks, pellets or other shapes. In certain aspects, the dried, porous implant body can define a reservoir for receiving amounts of a wetting liquid, e.g. to be used in the preparation of a putty or other malleable material from the dried implant material or used simply to wet the body for implant.

The dried porous body can be prepared using any suitable technique, including for example casting a liquid medium containing the dry ingredients, and then drying that medium by any appropriate means such as air drying or lyophilization. In this regard, the concentration of solids and other material in the liquid medium can be adjusted to control the ultimate porosity of the dried material, with lower solids concentrations typically providing higher porosities, and higher solids concentrations typically providing lower porosities. Additional variation of the porosity may be imparted by modifying the drying technique, including for example by modifying the lyophilization cycle to avoid substantial collapse or contraction of the cast material during drying. These and other porosity control parameters may be manipulated to control the porosity of the formed body.

Figure 1:
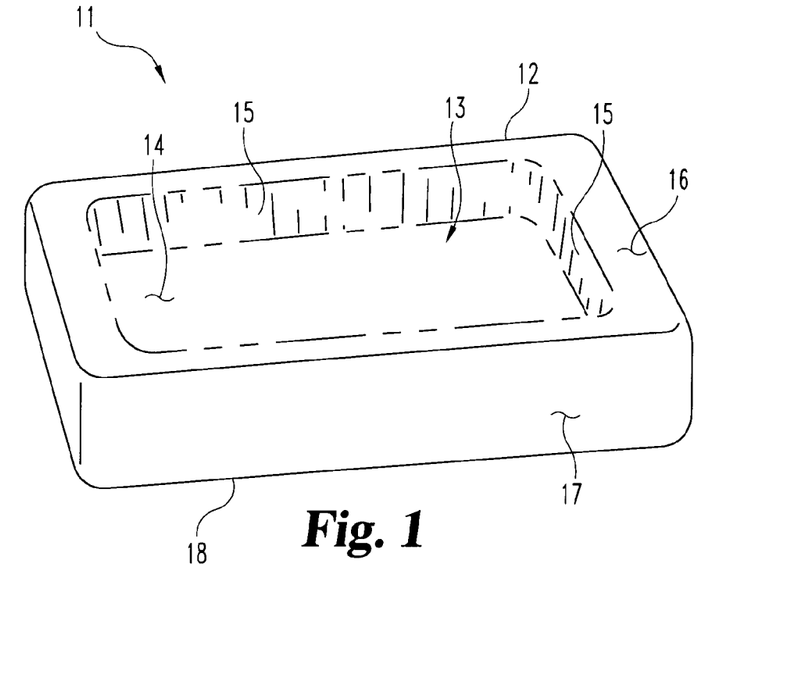
FIG. 1 provides a perspective view of a dried porous body implant material of the invention including a reservoir for receipt of a wetting liquid.

With reference now to FIG. 1, depicted is an illustrative, dried porous implant body 11 of the invention. The body 11 has a cast material 12 which defines a reservoir 13. The reservoir 13 has a bottom surface 14 and side walls 15, and can hold a liquid to be used to wet the body 11, for example in the formation of a putty or a wetted implant body, such that the liquid can be conveniently charged to reservoir 13 and allowed to soak into body 11 over time. The body 11 has an upper surface 16 surrounding the reservoir 13, as well as sidewalls 17 and a bottom surface 18.

Figure 2:
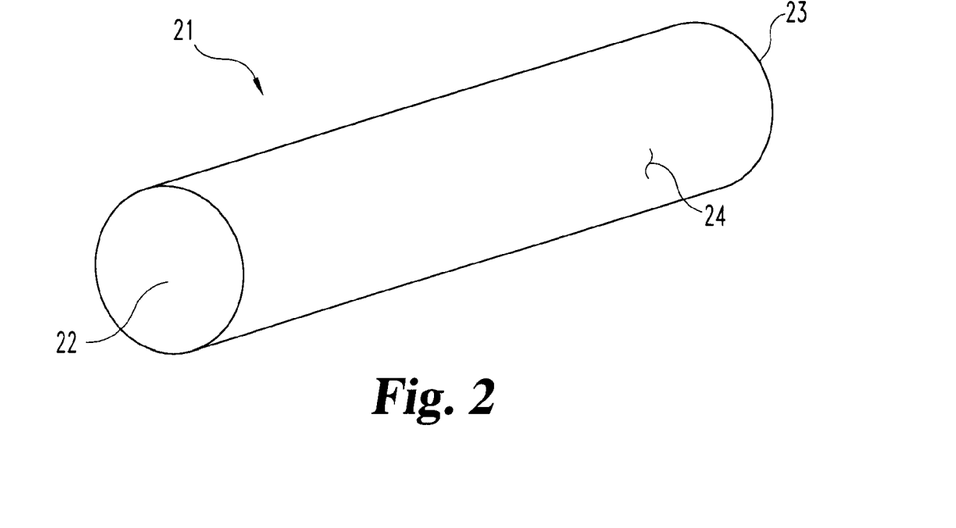
FIG. 2 provides a perspective view of a cylindrical-form dried porous body implant material of the invention.

Referring to FIG. 2, shown is another dried, porous implant body 21 according to one embodiment of the invention. Implant body 21 is cylindrical in shape, having a circular cross section. Implant body 21 is thus conveniently shaped for receipt within a cylindrical syringe barrel of a roughly corresponding or greater cross sectional dimension. Implant body 21 includes a first end 22, a second end 23, and a smooth, rounded external surface 24.

In certain modes of use, the dried, porous body (e.g. 11, 21) can be a disruptable body and can be combined with a sufficient amount of a liquid material such as an aqueous medium to prepare a putty or other malleable form material, e.g. as described herein. In these embodiments, the body (11, 21) will exhibit a disruptable character, such that it can be broken down by physical manipulation (e.g. manual crushing and kneading) to form a putty or other malleable material when combined with a liquid. Thus, chemical, covalent cross linking between the collagen materials in the disruptable dried material, if any, will generally be minimal. Other modes of providing integrity to the body (11, 21) can be used, e.g. dehydrothermal cross linking, or cross linking or adhesive forces imparted by ionic or hydrogen bonding. It will thus be understood that cross linking can be present in the dried, porous body (11, 21), but that it will be of such a nature to leave the body disruptable to form a malleable substance as described herein.

Typically, the combination of a disruptable, dried porous implant body of the invention with the liquid carrier, and the physical kneading or other mixing of the resultant mass, will result in a reduction of the volume of the dried porous body, for example resulting in a putty volume that is about 30% to about 70% of that of the original implant body, more typically about 40% to about 60%. This is a result of a breakdown of the original porosity of the dried implant body to form a relatively less porous or non-porous putty implant composition. The liquid carrier will typically be an aqueous substance, including for instance sterile water, physiological saline, blood, bone marrow, bone marrow fractions or other solutions (with or without organic co-solvents), emulsions or suspensions that provide adequate wetting characteristics to form putties of the invention.

Figure 3:
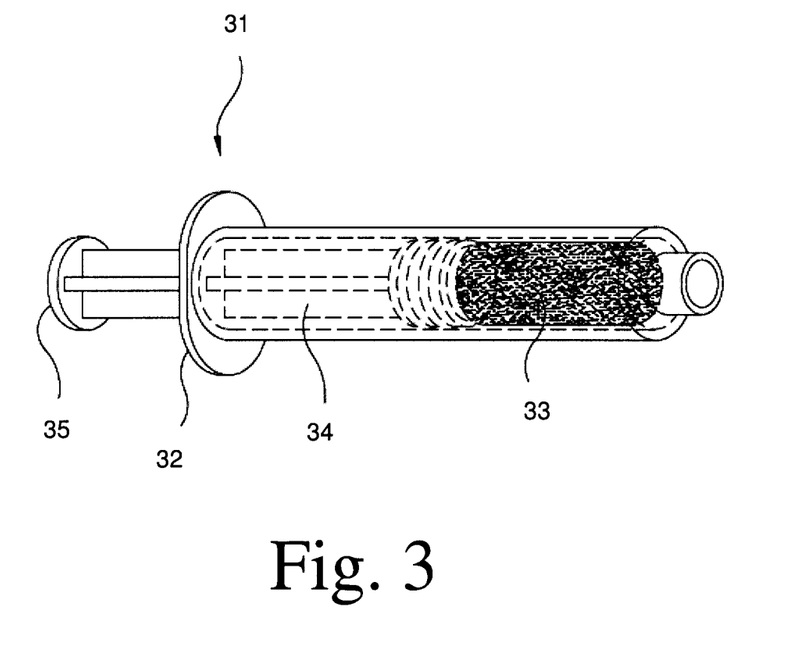
FIG. 3 provides a perspective view of a medical product of the invention including a medical paste or putty packaged within a terminally sterilized syringe device.

In certain embodiments, malleable compositions of the present invention can be manufactured in a ready-to-use format and packaged in a medically acceptable container for wetted malleable materials. In some embodiments, as illustrated in FIG. 3, the ready-to-use medical product can be a product 31 including a syringe device 32 containing an amount of a malleable composition 33 of the invention. The composition is contained within syringe barrel 34, and is transferable from the barrel 34 by actuating a plunger 35.

In use, the malleable or dimensionally-stable implant compositions of the invention can be implanted at a site at which bone growth is desired, e.g. to treat a disease, defect or location of trauma, and/or to promote artificial arthrodesis. The malleable form of certain inventive compositions enables their positioning, shaping and/or molding within voids, defects or other areas in which new bone growth is desired. In particularly advantageous embodiments, a shape-retaining putty material will provide sufficient three-dimensional integrity to resist substantial compression when impinged by adjacent soft tissues of the body at a bony implant site.

Bone repair sites that can be treated with compositions of the invention include, for instance, those resulting from injury, defects brought about during the course of surgery, infection, malignancy or developmental malformation. The compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the compositions include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Where a composition of the invention is osteogenic, once in place, it can effectively induce the ingrowth of bone into the desired area even in a human or other primate subject such as a human exhibiting a relatively slow rate of bone formation compared to smaller mammals, for example rodents or rabbits.

Osteogenic compositions of the invention are especially advantageous when used in bones or bone portions that are vascularized to only moderate or low levels. These areas present particularly low rates of bone formation, and as such the rapid resorption of the carrier poses enhanced difficulties. Examples of moderate or only slightly vascularized sites include, for example, transverse processes or other posterior elements of the spine, the diaphysis of long bones, in particular the mid diaphysis of the tibia, and cranial defects. An especially preferred use of compositions of the invention is as an implant to promote arthrodesis between vertebrae in spinal fusions in humans or other mammals, including for example interbody, posterior and/or posterolateral fusion techniques.

In addition, in accordance with other aspects of the invention, the malleable or other compositions of the invention can be incorporated in, on or around a load-bearing spinal implant (e.g. having a compressive strength of at least about 10000 N) implant device such as a fusion cage, dowel, or other device having a pocket, chamber or other cavity for containing an osteogenic composition, and used in a spinal fusion such as an interbody fusion. In one illustrative example, an inventive osteogenic composition can be used in conjunction with a load-bearing interbody spinal spacer to achieve an interbody fusion.

Medical compositions of the present invention can also be used in combination with cells, including for instance progenitor and/or stem cells derived from embryonic or adult tissue sources and/or taken from culture. Illustratively, compositions of the invention can incorporate cells derived from blood, bone marrow, or other tissue sources from the patient to be treated (autologous cells) or from a suitable allogenic or xenogenic donor source. In certain embodiments of the invention, putties of the invention incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, the implant materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into the putty material of the present invention, e.g. by using the fraction in or as the wetting medium for the dried, porous body as discussed hereinabove.

The present invention also provides medical kits that can be used to prepare implant compositions. Such kits can include a dried, porous body according to the invention, along with an aqueous medium for combination with the body to form malleable implant composition or another wetted implant form, and/or another item such as a load-bearing implant (e.g. a spinal spacer) and/or an osteogenic substance such as a BMP. In one specific form, such a medical kit will include the dried, porous body, a BMP in lyophilized form (e.g. rhBMP-2), and an aqueous medium for reconstitution of the BMP to prepare an aqueous formulation that can then be combined with the dried, porous body to prepare an osteogenic putty or other wetted implant form of the invention.

The invention will now be more particularly described with reference to the following specific Examples. It will be understood that these Examples are illustrative and not limiting of the invention.

Example 1

Preparation of Dried Implant Body

Sodium alginate is added with mixing to a preparation containing insoluble collagen fibers and soluble collagen adjusted with NaOH to have a pH in the range of 6.5-7.0. To this mixture are added biphasic calcium phosphate ceramic granules, with mixing. A dried, porous body is prepared by casting the resulting mixture into a cylindrical form and then lyophilizing the cast mixture. The dried body exhibits a porosity of about 85%. The relative amounts of the constituents of the dried body are as follows:

| Material | Wt % Solids |
| --- | --- |
| Biphasic CaP Granules (BCP)* | 75% |
| Insoluble Collagen Fibers | 15% |
| Acid Soluble Collagen | 5% |
| Sodium Alginate | 5% |

*Mastergraft ® Ceramic Granules, biphasic calcium phosphate granules containing 85% tricalcium phosphate and 15% hydroxyapatite, particle size 0.5-1.6 mm.

Example 2

Preparation of Osteoconductive Putty

Phosphate buffered saline (PBS) is added to the body of Example 1, and the body is disrupted and kneaded to form a malleable putty. The PBS is added in sufficient amount that water constitutes about 70% by weight of the formed putty. The formed putty contains about 0.3 g/cc biphasic calcium phosphate ceramic granules, 0.05 g/cc insoluble collagen fibers, 0.02 g/cc acid soluble collagen, and 0.02 g/cc alginate. The putty formed is a malleable, cohesive, fibrous mass with entrained ceramic granules.

Example 3

Preparation of Osteogenic Putty

A buffered aqueous solution of rhBMP-2 (1.5 mg/ml solution, as available with INFUSE® Bone Graft, Medtronic Sofamor Danek, Memphis, Tenn.) is added to the body of Example 1, and the body is disrupted and kneaded to form a malleable putty. The rhBMP-2 solution is added in sufficient amount that water constitutes about 70% by weight of the formed putty. The formed putty contains about 0.3 g/cc biphasic calcium phosphate ceramic granules, 0.05 g/cc insoluble collagen fibers, 0.02 g/cc acid soluble collagen, 0.02 g/cc alginate, and about 1.5 mg/ml of rhBMP-2. The putty formed is an osteogenic, malleable, cohesive, fibrous mass with entrained ceramic granules.

Example 4

Use of Inventive Putty in Interbody Spinal Fusions

An ovine interbody fusion model is used to compare the ability of a 5 mm×11 mm×11 mm polyetheretherketone spinal spacer (VERTE-STACK® CORNERSTONE® PSR PEEK Implant, Medtronic Sofamor Danek, Memphis, Tenn.) with packed-in Autograft and the PEEK spacer with packed-in Osteogenic Putty of Example 3 to effect interbody fusion at 6 months post-operatively. The efficacy of these treatments to induce interbody fusion in the ovine lumbar fusion model using blinded radiographic, biomechanical, and histologic measures is evaluated. Assessment of fusion is made with Faxitron high-resolution radiography, non-destructive biomechanical testing, and undecalcified histology with corresponding microradiography. All analyses are conducted in a blinded fashion. In addition, undecalcified histology is used to evaluate the osteocompatibility of the Example 3 Putty. In addition to the treatment groups being evaluated, normal spines are evaluated using the same methodology. When all data acquisition is complete, the key is broken, and radiographic, biomechanical, and histologic data are analyzed by treatment group.

Animal Model:

The sheep lumbar spine model is used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., *Spine:* 22(20): 2365-2374, 1997; and White AA and Panjabi MM, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

Upon arrival at the facility, the 12 sheep are placed in the appropriate pastures of the large animal research barn. They are dewormed and eartagged for identification. Physical examination is performed and any animals with signs of respiratory disease had venous blood submitted for a complete blood count (CBC).

The sheep are anesthetized. Wool is removed from the dorsal lumbar area and the sheep positioned in sternal recumbency on the operating table.

Iliac Crest Autograft Harvesting:

Autograft is used as a control. The following protocol is followed. The dorsal and dorsolateral lumbar and iliac crest areas are prepared for aseptic surgery with multiple scrubs of povidone-iodine alternated with isopropyl alcohol. The area is draped and a 3-cm incision made over the left iliac crest. Following partial reflection of the gluteal muscles, an osteotome is used to create a small window in the craniodorsal face of the iliac crest. Using a curette, about 2 cc of autogenous cancellous bone is removed, and is later packed into one of the implants (e.g. PEEK spacer) used for the lumbar fusion (this is the control case). Intralesional morphine sulfate is administered prior to closure of the iliac crest incision. The iliac crest site is closed routinely using 2/0 polysorb for the subcutaneous tissues and stainless steel staples for the skin.

Ventral ("Anterior") Interbody Fusion:

The dorsal and dorsolateral lumbar area is prepared for aseptic surgery with multiple scrubs of povidone-iodine alternated with isopropyl alcohol. The area is draped and a ventrolateral retroperitoneal approach to L3/L4 and L5/L6 through the oblique abdominal muscles to the plane ventral to the transverse processes is made.

Implant Insertion:

The bone graft from the iliac crest or the Example 3 Putty is placed into the PEEK spacer (~1.5 cc of material) and implanted into the disc space, following preparation of the endplates.

Wound Closure:

Routine closure of external abdominal muscular fascia (0 Polysorb (absorbable suture), subcutaneous tissue (2/0 Polysorb and skin (2/0 monofilament non-absorbable suture) is performed. Operative time for each animal is about 40 minutes. Perioperative antibiotics (Cephazolin sodium) are administered. Postoperative radiographs are performed while the sheep are still under general anesthesia.

Aftercare:

Immediately after surgery, the sheep are transferred from the operating table to a modified wheelbarrow and while still under general anesthesia, taken to a radiology suite where dorsoventral and lateral radiographs of the fusion sites are obtained. Following radiographic evaluation, while still in the modified wheelbarrow, they are observed until the swallowing reflex returns. At that point they are extubated and taken to a trailer where they are propped in sternal recumbency. At the end of the day, all animals that are operated upon that day are moved to research pastures. The sheep are housed outdoors (with access to a three-sided shelter) for the convalescence and allowed to exercise at will. Postoperative analgesia is provided as described. The sheep are anesthetized and radiographed at three months posoperatively.

Euthanasia:

After 6 months postoperatively, the 12 sheep are euthanized in a humane manner. Euthanasia is performed according to the guidelines set forth by the AVMA Panel on Euthanasia (J. Am. Vet. Med. Assoc., 202:229-249, 1993). Radiographs of the lumbar fusion sire are taken in these sheep to evaluate the degree of fusion at L3-L4.

Specimen Collection and Handling:

Following euthanasia, a complete gross necropsy is conducted on all 12 animals. Conventional gross examination of all major organ systems and histopathological evaluation of any pathological lesions is performed. Any animals that die or are prematurely euthanized during the course of the study have a complete necropsy performed to determine the cause of disease or death. At necropsy the lumbar vertebrae that are fused are harvested.

Material Analysis:

All samples from the lumbar area from the sheep are subjected to mechanical testing of the fusion sites. They are tested for stiffness to saggital and coronal plan bending moments (flexion, extension, right and left lateral bending). As these mechanical tests are nondestructive, the fusion sites are also examined histologically.

Implant Materials:

Twelve treated spinal levels (L4-L5) are evaluated. The study groups are defined below.

| Study Group | No. of Samples (N) |
| --- | --- |
| Autograft Interbody w/PEEK spacer (Autograft + PEEK) | 6 |
| Example 3 Putty w/PEEK spacer | 6 |
| Normal Intact | 17 |
| Total | 29 |

After the survival phase of the study is completed, the spines are immediately frozen for evaluation.

Methods of Analysis:

1. Ex-Vivo Biomechanical Testing of the Treated Lumbar Motion Segment:

Flexibility Testing

Unconstrained biomechanical testing is performed in a non-destructive manner on all spines after the frozen specimens are thawed. All tests are performed within 12 hours of specimen thawing. Specimens are only frozen once. Instrumentation applied to the anterior part of the vertebral body is removed prior to biomechanical testing so that only the stiffness of the spine and fusion mass construct is tested, not the instrumentation. Flexibility of the motion segments is determined in flexion, extension, right and left lateral bending, and right and left axial rotation. The purpose of the biomechanical testing is to quantify the stiffness of the lumbar motion segments augmented with the previously described interbody fusion treatments. The treated (L4-L5) motion segments are dissected from the harvested lumbar spines and cleaned of extraneous soft tissues leaving the ligamentous and osseous tissues intact. Specially designed loading and base frames are secured on the L4 and L5 vertebra, respectively.

Moments of 0, 0.5, 2.5, 4.5, 6.5, and 8.5 Nm are achieved in each loading direction. Static loads are used to apply the pure moments. Three markers reflecting the infrared light are attached to each vertebra. The locations of the infrared reflective markers are recorded using three VICON cameras (ViconPeak, Oxford, England) at each load. Three-dimensional load-displacement data are then acquired with pure moments applied in flexion, extension, left and right lateral bending, and left and right axial rotation. Basic principles of using 3-D motion analysis system for investigating the 3-D load-displacement behavior are well known in the literature.

Biomechanics data from a normal (untreated) intact group of sheep lumbar spine motion segments that have been obtained previously are used as baseline data for normal lumbar spine motion for L4-L5 in sheep. Differences in the stiffness (flexibility) between groups and the normals are statistically compared. Non-parametric Kruskal-Wallis and Mann-Whitney tests are used to analyze the biomechanics data.

2. Radiographic Assessment:

Radiographs are taken immediately after surgery (AP and lateral views), at regular post-operative intervals (AP and lateral views), and at the time of sacrifice (AP and lateral views). A high-resolution radiography unit (Faxitron, Hewlett Packard, McMinnville, Oreg.) and high-resolution film (EKTASCAN B/RA Film 4153, Kodak, Rochester, N.Y.) are used to produce a high-resolution PA and lateral radiograph of the harvested lumbar spines after biomechanical testing. Radiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the radiographs. These radiographs are also used to gross the samples for histologic analyses as outlined below.

Three blinded evaluators evaluate the resulting Faxitron radiographs for interbody fusion. On the lateral radiographs, the center of the disc space as well as the anterior and posterior margins are evaluated for fusion based on the following scoring method: 4=continuous bony bridging, 3=increased bone density, 2=lucency with some bony bridging, and 1=non-fusion. Lastly, based on both the P/A and lateral radiographs, the blinded evaluators rate an overall fusion score for the spinal level using the following criteria:

3=Solid interbody fusion with no radiolucencies in interbody space
   2=Probable fusion with radiolucencies in the interbody space
   1=Non-fusion with significant radiolucencies in the disc space with no evidence of superior to inferior bony bridging 3. Undecalcified Histology and Microradiography:

Processing and Stained Undecalcified Sections

In all of the treatment groups, the bisected spinal level is analyzed using undecalcified techniques (microradiographs and multiple stain). Differential staining along with qualitative optical microscopy is performed to assess bony bridging and extent of fusion associated with the autograft or the bone graft substitute packed within the PEEK spacers. Differential staining is used to evaluate the extent of fusion adjacent to and within the PEEK spacers, the host response to the PEEK spacer and Example 3 Putty (if present), the interface of the PEEK spacer, bone graft and Example 3 Putty incorporation, and bone remodeling within the fusion mass.

After Faxitron radiography, all spinal levels containing an implant are grossed in the following manner. Using the band saw, a coronal plane cut is made along the entire length of the spinal column at the anterior aspect of the pedicles leaving anterior tissues intact. Tissues posterior to the disc space are discarded. Next, the anterior column of the spinal level is bisected mid-sagittally to produce right and left halves. The entire disc space is left intact. The inferior half of the L4 anterior column adjacent to the treated level is retained. The superior half of the L5 anterior column adjacent to the treated level is retained. Right and left sagittal samples from the level are so labeled, fixed in formalin, and processed (sequentially dehydrated in alcohols, cleared in a xylene substitute, and embedded in graded catalyzed methyl methacrylate.

After polymerization is complete and the samples hardened, sectioning and staining is performed. The blocks containing the right and left halves of the treated aspect of the spinal level are sectioned in the sagittal plane on a low speed diamond saw (Buehler Isomet, Lake Bluff, Ill.). For all embedded tissue blocks, sagittal sectioning commence from the middle of the treated aspect of the spinal level to the lateral aspect of the treated area. Thus, section #1 from the "right block" is sampled in the middle of the fusion mass whereas section #6 from the "right block" is sampled at the far lateral aspect of the treated area. Weights are used to produce sections on the order of 300 µm. Approximately 5-10 sections are made in the sagittal plane through each half of the interbody space. If necessary, grinding is performed to obtain the desired thickness. The thickness of the sections is measured with a metric micrometer (Fowler, Japan). Differential staining using a trichrome stain is used to permit histological differentiation.

Stained undecalcified sections are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the stained undecalcified sections.

Section Fusion Criteria:

Undecalcified sections are evaluated for fusion in the center of the disc space or thrugrowth region of the device, in the anterior margin, and in the posterior margin. These anatomic locations for each section are considered to be fused only if continuous bony bridging is found from superior to inferior.

Level Fusion Criteria:

Based on all sections evaluated, the following criteria are used to determine if histologic fusion is present in the level. The spinal level is considered fused if greater than 50% of the sections (corresponding microradiographs are analyzed concurrently but not "counted twice" for fusion) show continuous bony bridging. A partial fusion exists if less than 50% of the sections (and corresponding microradiographs) show continuous bony bridging. A non-fusion exists if none of the sections and corresponding microradiographs show continuous bony bridging.

Microradiography:

Undecalcified sections from the treated lumbar spinal levels are radiographed using a microradiography unit (Faxitron radiography unit, Hewlett Packard, McMinnville, Oreg.) and spectroscopic film (B/RA 4153 film, Kodak, Rochester, N.Y.). The thickness of the sections is measured with a metric micrometer (Fowler, Japan) to determine the exposure time. Sections are labeled with ultra-fine permanent markers, placed on the Ektascan B/RA 4153 film, and exposed to the x-ray source at 20 kV and 3 mA for approximately 45 seconds for each 100 µm of section thickness. The film is then developed, fixed, and analyzed for ossification using standard optical microscopy. Microradiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the microradiographs.

Analysis of the sections and microradiographs is used to:
1) Evaluate the extent of fusion adjacent to and within the PEEK spacers, bone graft and Example 3 Putty incorporation, and bone remodeling within the fusion mass,
2) Determine the host response to the biomaterials used, and
3) Evaluate the interface of the PEEK spacer.

Example 5

Use of Osteogenic Putty in Posterolateral Fusion

An instrumented ovine posterolateral fusion model is used to evaluate the ability of Autograft and the Osteogenic Putty of Example 3 to effect posterolateral fusion at 6 months post-operatively. The efficacy of these treatments to induce posterolateral fusion in the ovine lumbar fusion model is evaluated using blinded radiographic, biomechanical, and histologic measures. Assessment of fusion is made with Faxitron high-resolution radiography, non-destructive biomechanical testing, and undecalcified histology with microradiography. All analyses are conducted in a blinded fashion. In addition, undecalcified histology is used to evaluate the osteocompatibility of the osteogenic putty. In addition to the treatment groups being evaluated, biomechanical properties of normal spines are evaluated using the same methodology. When all data acquisition is complete, the key is broken, and radiographic, biomechanic, and histologic data are analyzed by treatment group.

Animal Model:

The sheep lumbar spine model is used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., Spine: 22(20): 2365-2374, 1997; and White AA and Panjabi MM, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

12 sheep are placed in the appropriate pastures of the large animal research barn. They are dewormed and eartagged for identification. Physical examination is performed and any animals with signs of respiratory disease have venous blood submitted for a complete blood count (CBC).

The sheep are anesthetized. Wool is removed from the dorsal lumbar area and the sheep positioned in sternal recumbency on the operating table. The dorsal and dorsolateral lumbar area are prepared for aseptic surgery with multiple scrubs of povidone-iodine alternated with isopropyl alcohol. The area is draped and a dorsal approach to L3-L6 is made through the dorsal lumbar musculature.

Iliac Crest Autograft Harvesting:

Autograft is used as a control. The following protocol is followed. The dorsal and dorsolateral lumbar and iliac crest areas are prepared for aseptic surgery with multiple scrubs of povidone-iodine alternated with isopropyl alcohol. The area is draped and a 3-cm incision made over the left iliac crest. Following partial reflection of the gluteal muscles, an osteotome is used to create a small window in the craniodorsal face of the iliac crest. Using a curette, about 2 cc of autogenous cancellous bone is removed, and is later packed into one of the implants (e.g. PEEK spacer) used for the lumbar fusion (this is the control case). Intralesional morphine sulfate is administered prior to closure of the iliac crest incision. The iliac crest site is closed routinely using 2/0 polysorb for the subcutaneous tissues and stainless steel staples for the skin.

Dorsolateral ("posterolateral") Interbody Fusion:

The dorsal lumbar area is prepared for aseptic surgery with multiple scrubs of povidone-iodine alternated with isopropyl alcohol. The area is draped and local anesthesia (Bupivicaine) is infiltrated along the site of the intended incision for the dorsal approach to L3 and L4 and spinous processes.

Approach to the Transverse Processes:

A 20 cm. skin incision is made and the paraspinal muscles are dissected off the spinous processes and laminae. Facet joints and transverse processes between L3 and L4 are exposed.

Instrumentation and Spine Fusion Technique:

The transverse processes of L3 and L4 are decorticated bilaterally. The bone graft from the iliac crest or the osteogenic putty of Example 3 is placed between the transverse processes (~10 cc per side). The sheep now undergoes transpedicular screw fixation using screws and rods. The pedicle screws and rods are inserted at this point in the procedure.

Wound Closure:

Routine closure of external abdominal muscular fascia (0 Polysorb (absorbable suture), subcutaneous tissue (2/0 Polysorb and skin (2/0 monofilament non-absorbable suture) is performed. Operative time for each animal is about 50 minutes. Perioperative antibiotics (Cephazolin sodium) are administered. Postoperative radiographs are performed while the sheep are still under general anesthesia.

Aftercare:

Immediately after surgery, the sheep are transferred from the operating table to a modified wheelbarrow and while still under general anesthesia, and taken to a radiology suite where dorsoventral and lateral radiographs of the fusion sites are obtained. Following radiographic evaluation, while still in the modified wheelbarrow, they are observed until the swallowing reflex returns. At that point they are extubated and taken to a trailer where they are propped in sternal recumbency. At the end of the day, all animals that are operated upon that day are moved to research pastures. The sheep are housed outdoors (with access to a three-sided shelter) for the convalescence and allowed to exercise at will. Postoperative analgesia is provided as described. The sheep are anesthetized and radiographed at three months posoperatively.

Euthanasia:

After 6 months postoperatively, the 12 sheep are euthanized in a humane manner. Euthanasia is performed according to the guidelines set forth by the AVMA Panel on Euthanasia (J. Am. Vet. Med. Assoc., 202:229-249, 1993). Radiographs of the lumbar fusion sire are taken in these sheep to evaluate the degree of fusion at L3-L4.

Specimen Collection and Handling:

Following euthanasia, a complete gross necropsy is conducted on all 12 animals. Conventional gross examination of all major organ systems and histopathological evaluation of any pathological lesions is performed. Any animals that died or were prematurely euthanized during the course of the study have a complete necropsy performed to determine the cause of disease or death. At necropsy the lumbar vertebrae that are fused are harvested.

Material Analysis:

All samples from the lumbar area from the sheep are subjected to mechanical testing of the fusion sites. They are tested for stiffness to saggital and coronal plan bending moments (flexion, extension, right and left lateral bending). As these mechanical tests are nondestructive, the fusion sites are also examined histologically.

Implant Materials:

The study groups are defined below.

| | Study Group (per study design) | No. of Samples (N) |
|---|---|---|
| 1) | 10 cc/side Autograft (Autograft) | 6 |
| 2) | Example 3 Putty | 6 |
| 3) | Normal Intact | 17 |
| | Total | 28 |

At the completion of the survival phase of the animal study, the spines are immediately frozen for evaluation. The efficacy of the bone graft and bone graft substitutes to effect posterolateral fusion and bony healing is assessed by performing radiographic, biomechanical, and histologic analyses as detailed below. The study is performed in a blinded fashion. After all analyses are completed, the key is broken and radiographic, biomechanical, and histologic data are analyzed by treatment group.

Methods of Analysis:

1. Radiographic Assessment:

Radiographs are taken immediately after surgery, at regular post-operative intervals, and at the time of sacrifice. A Faxitron (Hewlett Packard, McMinnville, Oreg.) high-resolution radiography unit and high-resolution film (EKTAS-CAN B/RA Film 4153, Kodak, Rochester, N.Y.) is used to produce a high-resolution PA radiograph of the harvested lumbar spines after biomechanical testing. Radiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the radiographs. These radiographs are also used to gross the samples for histologic analyses as outlined below.

Three blinded evaluators evaluate the resulting Faxitron radiographs for intertransverse process fusion. On the PA radiograph, on both the right and left sides of the level, the intertransverse process space is evaluated for fusion based on the following scoring method: 4=continuous bony bridging, 3=increased bone density, 2=lucency with some bony bridging, and 1=non-fusion. Based on both the right and left sides of the PA radiographs, the blinded evaluators rate an overall fusion score for the spinal level using the following criteria:

1=Solid Fusion: Solid intertransverse process fusion on Right AND Left with no radiolucencies
2=Possible Fusion: Intertransverse process fusion on the Right OR Left, but not both. Lucencies in intertransverse process space on right or left.
3=Non-Fusion: Isolated bone formation without continuous superior to inferior bony bridging on both right and left sides. Significant lucency with no evidence of intertransverse process fusion on the right or left.

After the treatment code is broken, the radiographic fusion data are statistically analyzed.

2. Ex-Vivo Biomechanical Testing of the Treated Lumbar Motion Segment:

Flexibility Testing:

Unconstrained biomechanical testing is performed in a non-destructive manner on all spines after the frozen specimens are thawed. All metallic posterior instrumentation used to stabilize the posterolateral fusion is removed prior to biomechanical testing so that the stiffness of the spine and fusion mass construct is tested. Flexibility of the motion segments is determined in flexion, extension, right and left lateral bending, and right and left axial rotation. All tests are performed within 12 hours of specimen thawing. Specimens are only frozen once. The purpose of the biomechanical testing is to quantify the stiffness of the lumbar motion segments augmented with the previously described fusion treatments. The treated (L4-L5) motion segments are dissected from the harvested lumbar spines and cleaned of extraneous soft tissue leaving the ligamentous and osseous tissues intact. Specially designed loading and base frames are secured on the L4 and L5 vertebra, respectively.

Moments of 0, 0.5, 2.5, 4.5, 6.5, and 8.5 Nm are achieved in each loading direction. Static loads are used to apply the pure moments. A six-degree of freedom load cell is placed in series with the tested specimen to verify the applied moments. Three markers reflecting the infrared light are attached to each vertebra. The locations of the infrared reflective markers are recorded using three VICON cameras (Vicon Peak, Oxford, England) at each load. Three-dimensional load-displacement data are then acquired with pure moments applied in flexion, extension, left and right lateral bending, and left and right axial rotation. The three-dimensional coordinate data are analyzed to obtain the rotation angles of the superior vertebra with respect to the inferior vertebra and rotational flexibility of each motion segment.

Biomechanics data from a normal (untreated) intact group of sheep lumbar spine motion segments that have been obtained previously are used as baseline data for normal lumbar spine motion for L4-L5 in sheep. Differences in the stiffness (flexibility) between groups and the normals are statistically compared. Non-parametric Kruskal-Wallis and Mann-Whitney tests are used to analyze the biomechanics data.

3. Undecalcified Histology and Microradiography:

Processing and Stained Undecalcified Sections:

In each of the treatment groups, the bisected spinal intertransverse process spaces are analyzed using undecalcified techniques (microradiographs and multiple stain). Differential staining along with qualitative optical microscopy is performed to assess bony bridging and extent of fusion associated with autograft and the osteogenic putty of Example 3.

After Faxitron radiography, all spinal levels containing an implant are grossed in the following manner. The superior (L3-L4) and inferior (L5-L6) disc spaces are transected leaving the treated (L4-L5) functional spinal unit (FSU) intact. Using the band saw, a coronal plane cut is made along the entire length of the spinal column at the anterior aspect of the pedicles leaving posterior tissues intact. Anterior tissues are discarded. Next, the posterior elements of the spinal level are bisected mid-sagittally to produce right and left halves. An angled cut in the axial plane is made so that tissues cranial to the cranial transverse processes are discarded on the right and left sides. An angled cut in the axial plane is made so that tissues caudal to the caudal transverse processes are trimmed and discarded on the right and left sides. Tissues in the Right and Left intertransverse process spaces are further divided in the sagittal plane to produce a medial and lateral sample of the Left fusion mass as well as a medial and lateral sample of the Right fusion mass. Right and left medial and lateral samples are so labeled, fixed in formalin, and processed (sequentially dehydrated in alcohols, cleared in xylene or xylene substitute, and embedded in graded catalyzed methyl methacrylate).

After polymerization is complete and the samples hardened, sectioning and staining is performed. The blocks containing the transverse processes, autograft and Example 3 putty, and tissues in the transverse process space are sectioned in the sagittal plane on a low speed diamond saw (Buehler Isomet, Lake Bluff, Ill.). For the medial and lateral embedded tissue blocks described above, sectioning commences from the middle of the fusion mass for both the medial and lateral blocks. Thus, section #1 from the "right lateral block" is sampled in the middle of the fusion mass whereas section #6 from the "right lateral block" is sampled at the far lateral anatomic aspect of the fusion mass (tips of the transverse processes). Similarly, section #1 from the "right medial block" is sampled in the middle of the fusion mass whereas section #6 from the "right medial block" is sampled at the far medial anatomic aspect of the fusion mass (lamina and facet joints). Weights are used to produce sections on the order of 300 µm. Approximately 5-10 sections are made in the sagittal plane through each half of the intertransverse process space. If necessary, grinding is performed to obtain the desired thickness. The thickness of the sections is measured with a metric micrometer (Fowler, Japan). Differential staining using a trichrome stain is used to permit histological differentiation.

Stained undecalcified sections are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the stained undecalcified sections. Undecalcified histology sections and microradiographs for this study are scanned so that dorsal is at the top of the image. The ventral side of the section is usually flat and shows two oval transverse processes. Sections are scanned so that transverse processes are at the bottom (ventral aspect) of the image. A mm scale is scanned at the bottom (ventral aspect) of the image. Microsoft Photo editor is used to crop the images.

Section Fusion Criteria:

Undecalcified sections are considered fused if continuous bony bridging is found from superior to inferior in the section. If the presence of non-osseous tissues obviated continuous bony bridging, the section is further evaluated as follows. For non-fused sections, sections are classified as A) non-fusion with incomplete bridge, but with de novo bone found in >50% of the length of the section, or B) non-fusion with incomplete bridge, with de novo bone found in <50% of the length of the section.

Right and Left Side Level Fusion Criteria:

Based on all sections evaluated, the following criteria are used to determine if histologic fusion is present on the right or left side of the level. The right or left side of the spinal level is considered fused if greater than 50% (>50%) of the sections and corresponding microradiographs show continuous bony bridging. A partial fusion exists if 50% or less 50%) of the sections and corresponding microradiographs from the right or left side of the spinal level show continuous bony bridging. A non-fusion exists if none of the sections and corresponding microradiographs from the right or left side of the spinal level shows continuous bony bridging.

Microradiography:

Undecalcified sections from the treated lumbar spinal levels are radiographed using a microradiography unit (Faxitron radiography unit, Hewlett Packard, McMinnville, Oreg.) and spectroscopic film (B/RA 4153 film, Kodak, Rochester, N.Y.). The thickness of the sections is measured with a metric micrometer (Fowler, Japan) to determine the exposure time. Sections are labeled with ultra-fine permanent markers, placed on the Ektascan B/RA 4153 film, and exposed to the x-ray source at 20 kV and 3 mA for approximately 45 seconds for each 100 µm of section thickness. The film is then developed, fixed, and analyzed for ossification using standard optical microscopy. Microradiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the microradiographs.

Analysis of the sections and microradiographs is used to:
1) Evaluate histologic fusion,
2) Determine the host response to the autograft and bone graft substitutes, and
3) Estimate the quality and quantity of bone in the fusion mass within the intertransverse process space.

Example 6

Preparation of Additional Putties 6.1 Preparation of Dried Material

Using generally the procedures described in Example 1, dried porous bodies are prepared having the component combinations in the amounts shown in Table 1 below. Three series of dried bodies are prepared, Series A, B and C. The dried materials are prepared while adjusting the level of each component within the "Preferred Range" specified. More preferred materials results when using the "More Preferred" levels specified.

TABLE 1

| | % dry mass | |
|---|---|---|
| Component | Preferred Range | More Preferred |
| A Ceramic + Collagen + Alginate + PEG | | |
| BCP* | 40 to 90 | 62.5 |
| Insoluble Collagen Fibers | 5 to 25 | 10.4 |
| Sodium Alginate | 3 to 25 | 10.4 |
| Polyethylene Glycol (PEG)** | 1.5 to 25 | 16.7 |
| B Ceramic + Collagen + Alginate + Starch + PEG | | |
| BCP* | 40 to 90 | 62.5 |
| Insoluble Collagen Fibers | 5 to25 | 9.2 |
| Sodium Alginate | 5 to 25 | 2.5 |
| Potato Starch** | 5 to 25 | 9.2 |
| PEG** | 1.5 to 25 | 16.7 |
| C Ceramic + Collagen + Starch +/− PEG | | |
| BCP* | 40 to 90 | 73.9 |
| Collagen | 5 to 25 | 12.3 |
| Potato Starch | 5 to 25 | 12.3 |
| PEG** | 0 to 10 | 1.5 |

*Mastergraft ® Ceramic Granules, biphasic calcium phosphate granules containing 85% tricalcium phosphate and 15% hydroxyapatite, particle size 0.5-1.6 mm.
**PEG Molecular weight = 2000.

6.2 Preparation of Osteoconductive Putties from Dried Materials

Phosphate buffered saline (PBS) is added to the dried implant bodies prepared in accordance with Table 1, and the bodies are disrupted and kneaded to form a malleable putty. The PBS is added in an amount of about 0.5 cc's per gram of the dried implant body. The resulting putties provide an osteoconductive materials useful as bone void fillers or to otherwise treat bone defects as disclosed herein. The presence of PEG and/or starch significantly enhances the wettability of the alginate-containing dried bodies.

6.3 Preparation of Osteoinductive Putties from Dried Materials

A buffered aqueous solution of rhBMP-2 (1.5 mg/ml solution, as available with INFUSE® Bone Graft, Medtronic Sofamor Danek, Memphis, Tenn.) is added to the bodies prepared in accordance with Table 1, and the bodies are disrupted and kneaded to form a malleable putty. The rhBMP-2 solution is added in an amount of about 0.5 cc's per gram of the dried implant body. The resulting putties provide an osteoinductive materials useful to treat bone defects as disclosed herein. Again, the presence of PEG and/or starch significantly enhances the wettability of the alginate-containing dried bodies.

6.4 Preparation of Wet-Packaged Osteoconductive or Osteoinductive Putties

In alternative embodiments, the wet mixing procedures of Section 6.1 above are carried out, and the resulting putty materials are directly packaged wet in a syringe, vial or other suitable medical container, and terminally sterilized. In the case of osteoinductive putties, the solution(s) added during the mixing procedure contain the rhBMP-2. Additionally, the use of PEG in such wet-packaged products is optional.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for preparing an implantable osteogenic medical material, comprising: providing a dried, porous material that includes a particulate mineral material embedded within a disruptable matrix, said matrix comprising insoluble collagen, soluble collagen and a polysaccharide component, the polysaccharide component including one or more polysaccharide compounds comprising dextran, the polysaccharide component at a level of about 0.01 g/cc to about 0.2 g/cc, and one or more ionic polysaccharide compounds; applying an aqueous medium to the dried, porous material and disrupting the matrix so as to prepare a malleable, cohesive, shape-retaining putty that comprises 40% to 75% by weight of water, and applying a cationic gelling agent to the one or more ionic polysaccharide compounds to form an anionically-cross-linked gel with one or more divalent or trivalent cations, wherein the aqueous medium comprises polyethylene glycol, and the particulate mineral material is embedded within the disruptable matrix at a level of about 0.25 g/cc to about 0.55 g/cc, and the insoluble collagen particles are at a level of about 0.04 g/cc to about 0.15 g/cc.

2. The method of claim 1, wherein the aqueous medium includes a bone morphogenic protein dissolved therein at a level of about 0.6 mg/cc to about 2 mg/cc.

3. The method of claim 1, wherein: the particulate mineral material constitutes about 70% to 90% by weight of the dried, porous material; the insoluble collagen constitutes about 1% to about 15% of the dried, porous material; and the polysaccharide component constitutes about 1% to about 15% of the dried, porous material.

4. The method of claim 1, wherein the particulate mineral material comprises biphasic calcium phosphate having a weight ratio of tricalcium phosphate to hydroxyapatite of about 70:30 to about 95:5; and the insoluble collagen to soluble collagen are at a weight ratio of 75:25 to about 65:35.

* * * * *

UNITED STATES PATENT AND TRADEMARK OFFICE
CERTIFICATE OF CORRECTION

PATENT NO. : 9,730,982 B2
APPLICATION NO. : 14/492957
DATED : August 15, 2017
INVENTOR(S) : McKay et al.

Page 1 of 1

It is certified that error appears in the above-identified patent and that said Letters Patent is hereby corrected as shown below:

In the Specification

In Column 21, Line 57, delete "1 =" and insert -- 3 = --, therefor.

In Column 21, Line 62, delete "3 =" and insert -- 1 = --, therefor.

In Column 23, Line 63, delete "50%)" and insert -- ($\leq$ 50%) --, therefor.

Signed and Sealed this
Twenty-ninth Day of May, 2018

Andrei Iancu
*Director of the United States Patent and Trademark Office*